US012599449B2

(12) United States Patent
Baer

(10) Patent No.: US 12,599,449 B2
(45) Date of Patent: Apr. 14, 2026

(54) SURGICAL ROBOTIC SYSTEM WITH ORIENTATION SETUP DEVICE AND METHOD

(71) Applicant: Covidien LP, Mansfield, MA (US)

(72) Inventor: Michael Baer, Munich (DE)

(73) Assignee: Covidien LP, Mansfield, MA (US)

( * ) Notice: Subject to any disclaimer, the term of this patent is extended or adjusted under 35 U.S.C. 154(b) by 228 days.

(21) Appl. No.: 18/294,247

(22) PCT Filed: Aug. 16, 2022

(86) PCT No.: PCT/IB2022/057674
§ 371 (c)(1),
(2) Date: Feb. 1, 2024

(87) PCT Pub. No.: WO2023/021423
PCT Pub. Date: Feb. 23, 2023

(65) Prior Publication Data
US 2024/0341878 A1 Oct. 17, 2024

Related U.S. Application Data

(60) Provisional application No. 63/235,302, filed on Aug. 20, 2021.

(51) Int. Cl.
*A61B 34/35* (2016.01)
*A61B 34/20* (2016.01)
*A61B 90/98* (2016.01)

(52) U.S. Cl.
CPC .............. *A61B 34/35* (2016.02); *A61B 90/98* (2016.02); *A61B 2034/2059* (2016.02)

(58) Field of Classification Search
CPC . A61B 90/98; A61B 2034/2059; A61B 34/20; A61B 90/90; A61B 34/30–34/37; A61B 34/70–34/77
See application file for complete search history.

(56) References Cited

U.S. PATENT DOCUMENTS

| | | |
|---|---|---|
| 6,132,368 A | 10/2000 | Cooper |
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |

(Continued)

FOREIGN PATENT DOCUMENTS

| | | |
|---|---|---|
| WO | 2020113030 A1 | 6/2020 |
| WO | 2020214193 A1 | 10/2020 |

OTHER PUBLICATIONS

International Search Report and Written Opinion of the International Searching Authority issued in corresponding application PCT/IB2022/057674 mailed Nov. 30, 2022 (12 pages).

*Primary Examiner* — Jonathan T Kuo
(74) *Attorney, Agent, or Firm* — Carter, DeLuca & Farrel

(57) ABSTRACT
A surgical robotic system includes: a plurality of movable carts oriented relative to the surgical table, each of which includes a robotic arm, and an orientation device for calculating an orientation angle of each robotic arm relative to the surgical table.

20 Claims, 6 Drawing Sheets

(56) References Cited

U.S. PATENT DOCUMENTS

| | | |
|---|---|---|
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,433,389 B2 * | 4/2013 | Geiger .................. A61B 90/50 600/407 |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |

(56) References Cited

U.S. PATENT DOCUMENTS

| | | | |
|---|---|---|---|
| 8,864,752 | B2 | 10/2014 | Diolaiti et al. |
| 8,903,546 | B2 | 12/2014 | Diolaiti et al. |
| 8,903,549 | B2 | 12/2014 | Itkowitz et al. |
| 8,911,428 | B2 | 12/2014 | Cooper et al. |
| 8,912,746 | B2 | 12/2014 | Reid et al. |
| 8,944,070 | B2 | 2/2015 | Guthart |
| 8,989,903 | B2 | 3/2015 | Weir et al. |
| 9,002,518 | B2 | 4/2015 | Manzo |
| 9,014,856 | B2 | 4/2015 | Manzo et al. |
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,165 | B2 | 10/2018 | Power |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,405,934 | B2 | 9/2019 | Prisco et al. |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |
| 10,881,469 | B2 | 1/2021 | Robinson |
| 10,881,473 | B2 | 1/2021 | Itkowitz et al. |
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |

(56)  References Cited

U.S. PATENT DOCUMENTS

| | | | |
|---|---|---|---|
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs, II et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,161,248 B2 * | 11/2021 | Popovic | G05B 19/4155 |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 11,376,002 B2 | 7/2022 | Shelton, IV et al. | |
| 11,376,098 B2 | 7/2022 | Shelton, IV et al. | |
| 11,381,759 B2 | 7/2022 | Zhao et al. | |
| 11,382,621 B2 | 7/2022 | Scheib et al. | |
| 11,382,624 B2 | 7/2022 | Harris et al. | |
| 11,382,625 B2 | 7/2022 | Huitema et al. | |
| 11,382,626 B2 | 7/2022 | Shelton, IV et al. | |
| 11,382,627 B2 | 7/2022 | Huitema et al. | |
| 11,382,638 B2 | 7/2022 | Harris et al. | |
| 11,382,644 B2 | 7/2022 | Schoettgen et al. | |
| 11,389,160 B2 | 7/2022 | Shelton, IV et al. | |
| 11,389,255 B2 | 7/2022 | DiMaio et al. | |
| 11,399,906 B2 | 8/2022 | Shelton, IV et al. | |
| 11,406,379 B2 | 8/2022 | Hess et al. | |
| 11,410,259 B2 | 8/2022 | Harris et al. | |
| 11,419,630 B2 | 8/2022 | Yates et al. | |
| 11,424,027 B2 | 8/2022 | Shelton, IV | |
| 11,432,888 B2 | 9/2022 | Diolaiti et al. | |
| 11,432,893 B2 | 9/2022 | Itkowitz et al. | |
| 11,432,895 B2 | 9/2022 | Loh et al. | |
| 11,439,390 B2 | 9/2022 | Patel et al. | |
| 11,439,391 B2 | 9/2022 | Bruns et al. | |
| 11,468,791 B2 | 10/2022 | Jarc et al. | |
| 11,471,155 B2 | 10/2022 | Shelton, IV et al. | |
| 11,471,221 B2 | 10/2022 | Zhao et al. | |
| 11,478,308 B2 | 10/2022 | Hoffman et al. | |
| 11,490,977 B2 | 11/2022 | Schena et al. | |
| 11,497,499 B2 | 11/2022 | Shelton, IV et al. | |
| 11,504,119 B2 | 11/2022 | Shelton, IV et al. | |
| 11,504,124 B2 | 11/2022 | Patel et al. | |
| 11,510,743 B2 | 11/2022 | Shelton, IV et al. | |
| 11,517,312 B2 | 12/2022 | Wixey | |
| 11,517,325 B2 | 12/2022 | Shelton, IV et al. | |
| 11,518,048 B2 | 12/2022 | Saraliev et al. | |
| 2011/0028992 A1 * | 2/2011 | Geiger | A61B 90/50 606/130 |
| 2015/0272696 A1 | 10/2015 | Fry et al. | |
| 2017/0079730 A1 | 3/2017 | Azizian et al. | |
| 2019/0047151 A1 * | 2/2019 | Popovic | G05B 19/4155 |
| 2020/0268454 A1 | 8/2020 | Walter et al. | |
| 2023/0301732 A1 * | 9/2023 | Nikou | A61B 34/32 |

* cited by examiner

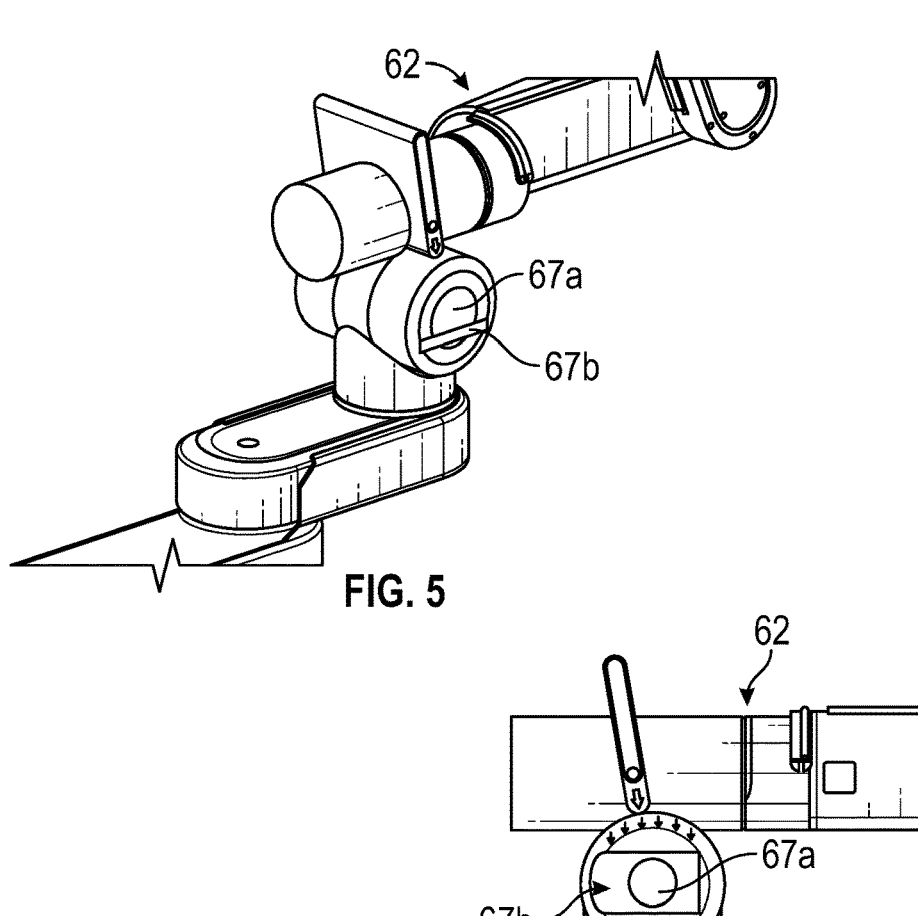
FIG. 5
FIG. 6
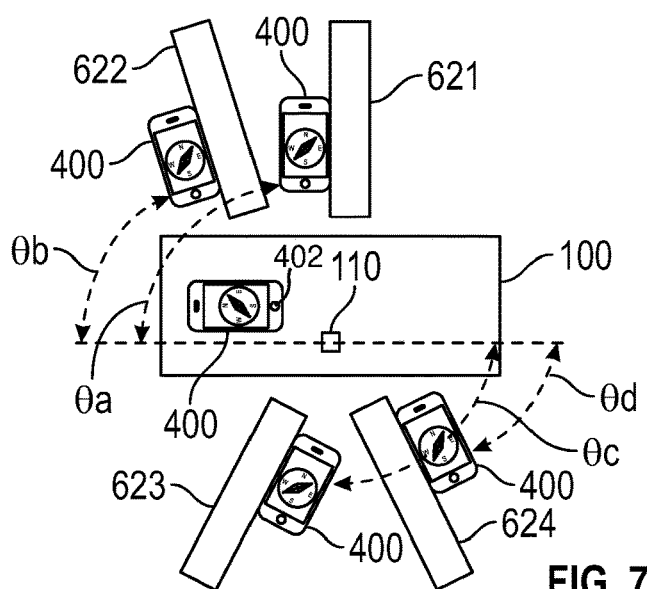
FIG. 7

SURGICAL ROBOTIC SYSTEM WITH ORIENTATION SETUP DEVICE AND METHOD

CROSS REFERENCE TO RELATED APPLICATIONS

The present application is a U.S. National Stage Application filed under 35 U.S.C. § 371(a) of International Patent Application No. PCT/IB2022/057674, filed on Aug. 16, 2022, which claims the benefit of and priority to U.S. Patent Provisional Application No. 63/235,302, filed on Aug. 20, 2021. The entire disclosures of the foregoing applications are incorporated by reference herein.

FIELD

The present disclosure generally relates to a surgical robotic system having one or more modular arm carts each of which supports a robotic arm and a surgical console for controlling the carts and their respective arms. More particularly, the present disclosure is directed to a system and method for registration of the modular arm carts in a surgical robotic system in relation to a surgical table.

BACKGROUND

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

Prior to utilizing the robotic arm, the robotic arm and the movable cart supporting the robotic arm need to be oriented around a surgical table and the orientation of the robotic arm must be known to properly control movement of the robotic arm relative to the surgical table. Thus, there is a need for a system to properly identify the orientation and placement of the robotic arms in the surgical operating room.

SUMMARY

According to one embodiment of the present disclosure, a surgical robotic system includes a movable cart, an orientation device, and a surgical console. The movable cart is positioned relative to a surgical table and includes a setup arm and a robotic arm. The orientation device includes a memory and a computer and is configured to store a zero position of the surgical table upon being placed at the zero position, link with the robotic arm, store a position of the setup arm upon being placed at the position of the setup arm, and calculate an orientation angle between the setup arm and the surgical table based on the stored zero position of the surgical table and the stored position of the setup arm. The surgical console includes an input device communicatively coupled to the robotic arm and is configured to control movement of the robotic arm and correlate the calculated orientation angle of the setup arm with movements of the input device for controlling movement of the robotic arm.

In an aspect, the setup arm includes an identification device readable by the orientation device for linking the orientation device to the setup arm and the identification device includes at least one of a near field communication chip or an optically readable code.

In an aspect, the setup arm includes an alignment member configured to align the orientation device to the setup arm upon placement of the orientation device at the position of the setup arm.

In an aspect, the surgical console is configured to determine whether two adjacent robotic arms are distanced a predetermined distance apart based on the calculated orientation angle of the setup arm.

In another aspect of the present disclosure, a surgical robotic system includes a surgical table, a first movable cart, a second movable cart, and an orientation device. The first movable cart is positioned relative to the surgical table and includes a first setup arm and the second movable cart positioned relative to the surgical table and includes a second setup arm. The orientation device includes a memory and a computer and is configured to store a zero position of the surgical table upon being placed at the zero position, link with the first setup arm, store a position of the first setup arm upon being placed at the position of the first setup arm, calculate an orientation angle between the first setup arm and the surgical table based on the stored zero position of the surgical table and the stored position of the first setup arm, link with the second setup arm, store a position of the second setup arm upon being placed at the position of the second setup arm, and calculate an orientation angle between the second setup arm and the surgical table based on the stored zero position of the surgical table and the stored position of the second setup arm.

In an aspect, the first setup arm includes a first identification device readable by the orientation device for linking the orientation device to the first setup arm and the second setup arm includes a second identification device readable by the orientation device for linking the orientation device to the second setup arm.

In an aspect, the first identification device and the second identification device include at least one of a near field communication chip or an optically readable code.

In an aspect, the first movable cart includes a first brake and the second movable cart includes a second brake.

In an aspect, the surgical robotic system further includes a cart controller in communication with the orientation device. The cart controller is configured to identify the first movable cart as registered in response to the first brake being engaged and receipt of the orientation angle of the first setup arm, and identify the second movable cart as registered in response to the second brake being engaged and receipt of the orientation angle of the second setup arm.

In an aspect, the first setup arm includes a first alignment member configured to align the orientation device to the first setup arm upon placement of the orientation device at the position of the first setup arm and the second setup arm includes a second alignment member configured to align the orientation device to the second setup arm upon placement of the orientation device at the position of the second setup arm.

In an aspect, the surgical robotic system further includes a surgical console including an input device communicatively coupled to a first robotic arm of the first movable cart and second robotic arm of the second movable cart. The surgical console is configured to receive the calculated orientation angle of the first setup arm and the calculated orientation angle of the second setup arm from the orientation device, correlate the calculated orientation angle of the first setup arm with movements of the input device for controlling movement of the first robotic arm, and correlate the calculated orientation angle of the second setup arm with movements of the input device for controlling movement of the second robotic arm.

In an aspect, the computer is configured to determine whether the first movable cart and the second movable cart are spaced apart by a predetermined distance based on the orientation angle of the first setup arm and the orientation angle of the second setup arm.

In another aspect of the present disclosure, a method of registering a setup arm with a surgical table is provided. The method includes placing a first movable cart and a second movable cart around a surgical table, the first movable cart including a first setup arm and the second movable cart including a second setup arm, placing an orientation device at a zero position on the surgical table and storing the zero position in a memory of the orientation device, moving the orientation device from the zero position to the first setup arm, linking the orientation device to the first setup arm, calculating, by a computer of the orientation device, an orientation angle of the first setup arm relative to the surgical table, moving the orientation device from the first setup arm to the second setup arm, linking the orientation device to the second setup arm, and calculating, by the computer of the orientation device, an orientation angle of the second setup arm relative to the surgical table.

In an aspect, the first setup arm includes a first identification device readable by the orientation device for linking the orientation device to the first setup arm and the second setup arm includes a second identification device readable by the orientation device for linking the orientation device to the second setup arm.

In an aspect, the first identification device and the second identification device include at least one of a near field communication chip or an optically readable code.

In an aspect, the first movable cart includes a first brake and the second movable cart includes a second brake.

In an aspect, the method further includes identifying the first movable cart as registered in response to the first brake being engaged and receipt of the orientation angle of the first setup arm, and identifying the second movable cart as registered in response to the second brake being engaged and receipt of the orientation angle of the second setup arm.

In an aspect, the method further includes determining whether the first movable cart and the second movable cart are spaced apart by a predetermined distance based on the orientation angle of the first setup arm and the orientation angle of the second setup arm.

In an aspect, the first setup arm includes a first alignment member configured to align the orientation device to the first setup arm upon placement of the orientation device at the position of the first setup arm and the second setup arm includes a second alignment member configured to align the orientation device to the second setup arm upon placement of the orientation device at the position of the second setup arm.

In an aspect, the method further includes delivering the calculated orientation angle of the first setup arm and the calculated orientation angle of the second setup arm to a surgical console including an input device configured to control movement of a first robotic arm of the first movable cart and a second robotic arm of the second movable cart, correlating the calculated orientation angle of the first setup arm with movements of the input device for controlling movement of the first robotic arm, and correlating the calculated orientation angle of the second setup arm with movements of the input device for controlling movement of the second robotic arm.

BRIEF DESCRIPTION OF THE DRAWINGS

Various embodiments of the present disclosure are described herein with reference to the drawings wherein:

FIG. 5 is a perspective view of the setup arm and the surgical robotic arm of the surgical robotic system of FIG. 1 according to the present disclosure;

FIG. 6 is a side view of the setup arm and the surgical robotic arm of the surgical robotic system of FIG. 1 according to the present disclosure;

FIG. 7 is a schematic diagram of four setup arms positioned relative to a surgical table of the surgical robotic system of FIG. 1 according to the present disclosure.

DETAILED DESCRIPTION

Figure 1:
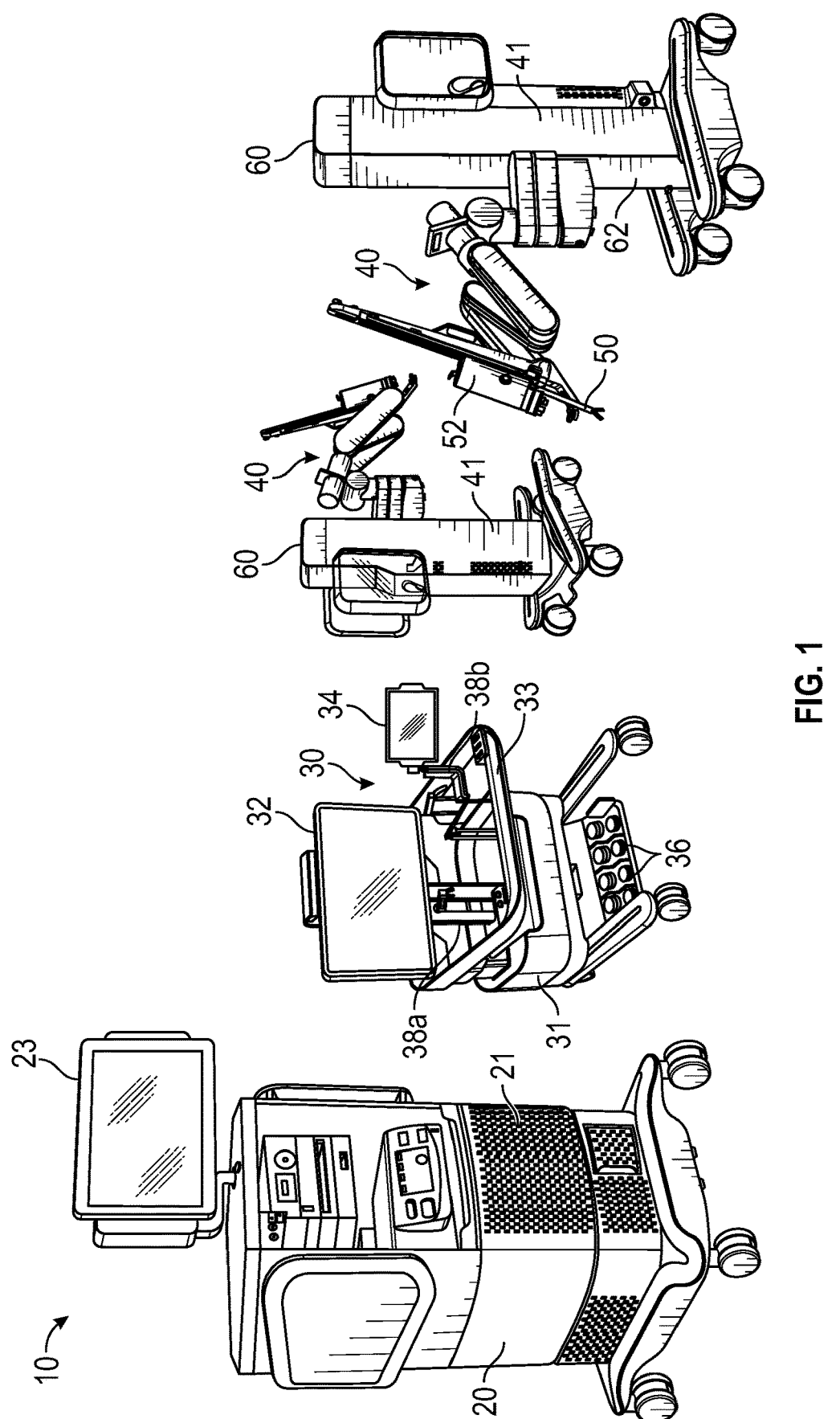
FIG. 1 is a schematic illustration of a surgical robotic system including a control tower, a console, and one or more surgical robotic arms according to the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IOT device, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscope camera 51, configured to provide a video feed for the user. In further embodiments, the surgical instrument 50 may be an electrosurgical forceps configured to seal tissue by compression tissue between jaw members and applying electrosurgical current thereto. In yet further embodiments, the surgical instrument 50 may be a surgical stapler including a pair of jaws configured to grasp and clamp tissue whilst deploying a plurality of tissue fasteners, e.g., staples, and cutting stapled tissue.

One of the robotic arms 40 may include a camera 51 configured to capture video of the surgical site. The surgical console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of handle controllers 38a and 38b which are used by a user to remotely control robotic arms 40. The surgical console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
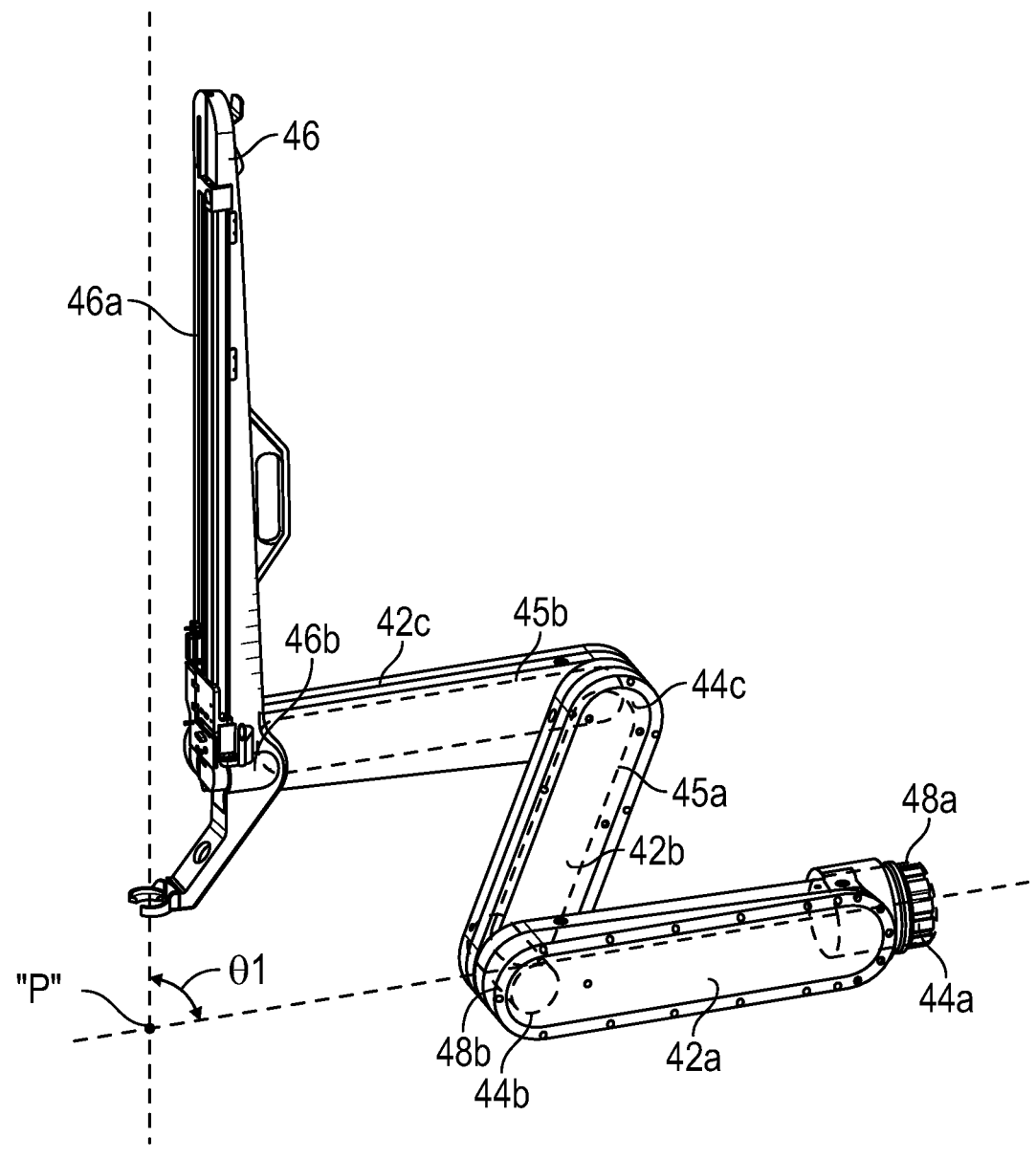
FIG. 2 is a perspective view of a surgical robotic arm of the surgical robotic system of FIG. 1 according to the present disclosure.
Figure 3:
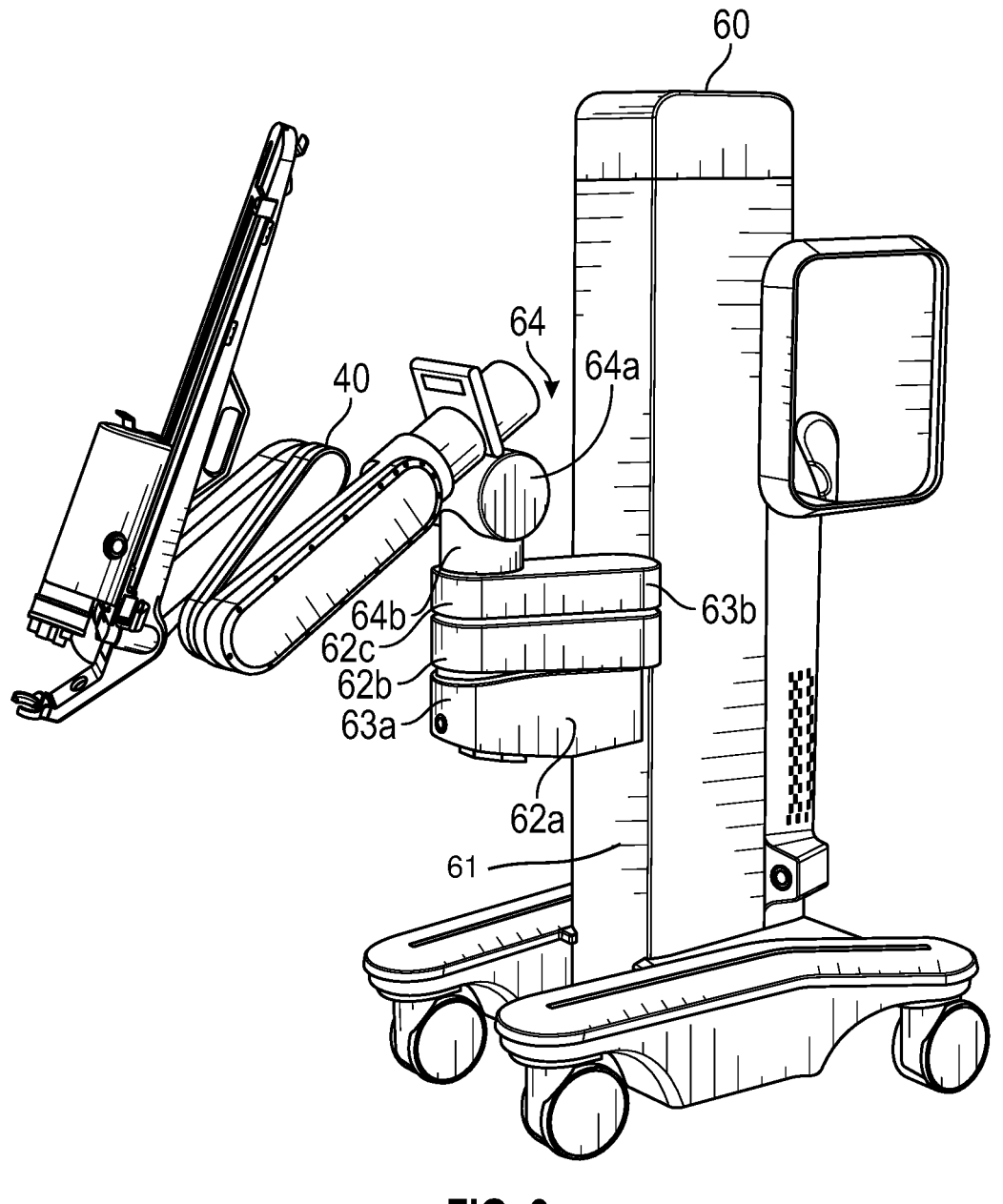
FIG. 3 is a perspective view of a setup arm with the surgical robotic arm of the surgical robotic system of FIG. 1 according to the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62a and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table 100 (FIG. 7). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effectors) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c.

The robotic arm 40 also includes a plurality of manual override buttons 53 disposed on the IDU 52 and the setup arm 62, which may be used in a manual mode. The user may press one or the buttons 53 to move the component associated with the button 53.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ1 between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ1. In embodiments, some or all of the joints 44a, 44b, 44c may include an actuator to obviate the need for mechanical linkages.

Figure 4:
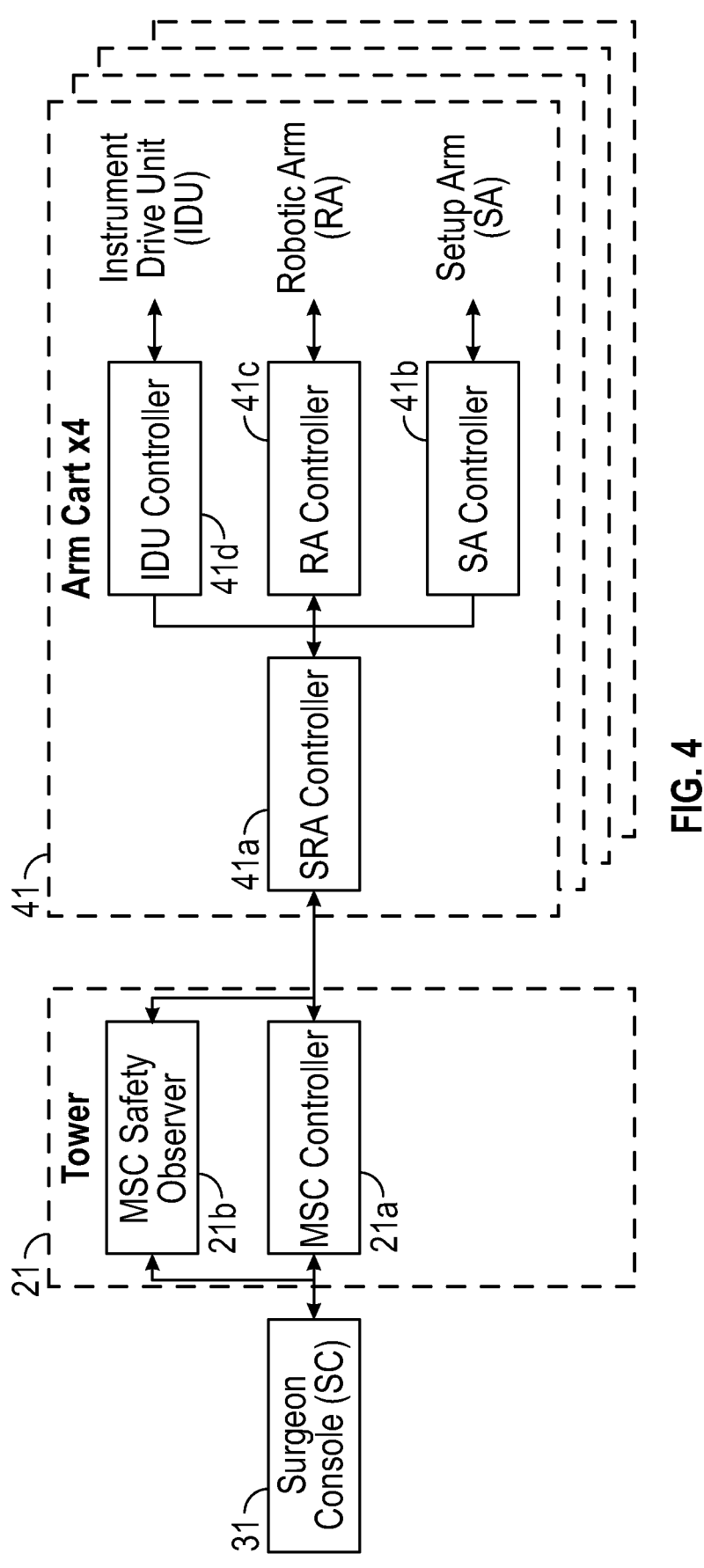
FIG. 4 is a schematic diagram of a computer architecture of the surgical robotic system of FIG. 1 according to the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled as follows. Initially, a pose of the handle controller controlling the robotic arm 40, e.g., the handle controller 38a, is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In embodiments, the coordinate position is scaled down and the orientation is scaled up by the scaling function. In addition, the controller 21a also executes a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

With reference to FIGS. 5-8, the surgical robotic system 10 (FIG. 1) includes an orientation device 400 which is used for calculating the orientation of each setup arm 62 of each robotic arm 40 relative to the surgical table 100. The orientation device 400 includes a memory and a processor configured to execute software and is communicatively coupled to the computers 21, 31, and 41 of the control tower 20, the surgical console 30, and the robotic arm 40 and allows for the transfer of data and information to and from the orientation device 400 and the control tower 20, the surgical console 30, and the robotic arm 40. In embodiments, the orientation device 400 may have a wired connection (e.g., USB), or may include a wireless transmitter/receiver in wireless communication with the control tower 20 and/or surgical console 30, which also may include a wireless transmitter/receiver. The wireless communication may be radio frequency, optical, WiFi®, Bluetooth® (an open wireless protocol for exchanging data over short distances using short length radio waves), etc. The control tower 20 and/or surgical console 30 may transfer data and/or real-time data from the orientation device 400. The control tower 20 or the surgical console 30 utilizes this information to correlate movement of the robotic arm 40, relative to the surgical table 100, with movements of input devices, e.g., handle controllers 38a, 38b, from the surgical console 30. In embodiments, the orientation device 400 may include a camera 402. The orientation device 400 is configured to either calculated the orientation angles of the setup arms 62 or acquire data for delivery to another component of the surgical robotic system 10 (e.g. one or more of computers 21, 31, 41) so that another component of the surgical robotic system 10 (e.g., one or more of computers 21, 31, 41) may calculate the orientation angles of the setup arms 62.

FIG. 7 illustrates an example configuration utilizing four setup arms 62, referred to individually as first setup arm 621, second setup arm 622, third setup arm 623, and fourth setup arm 624, but any number of setup arms 62 may be utilized with the surgical robotic system 10 depending on the particular need for the procedure being performed. Each setup arm 62 includes an identification device 67a, which is readable by the orientation device 400 to identify the particular setup arm 62, and an alignment member 67b which enables proper alignment of the orientation device 400 to the setup arm 62. The identification device 67a may be any suitable device readable by the orientation device 400, for example a near field communication tag, RFID tag, or optically readable tag (e.g., QR code, bar code, etc.). Thus, the orientation device 400 may include a scanning device, such as the camera 402 to read the identification device 67a of the setup arm 62, or a user may manually enter the identification information of the setup arm 62 to link the orientation device 400 to the specific setup arm 62 when appropriate.

Referring to FIG. 6 specifically, alignment member 67b is shown as a recess formed in the housing of the setup arm 62 for receiving the orientation device 400, however alignment member 67b may include any suitable structure capable of assisting in ensuring the proper alignment of the orientation device 400 against the setup arm 62, such as a recess, protrusion, ledge, and/or magnetic-based or sensor-based orientation elements.

Figure 8:
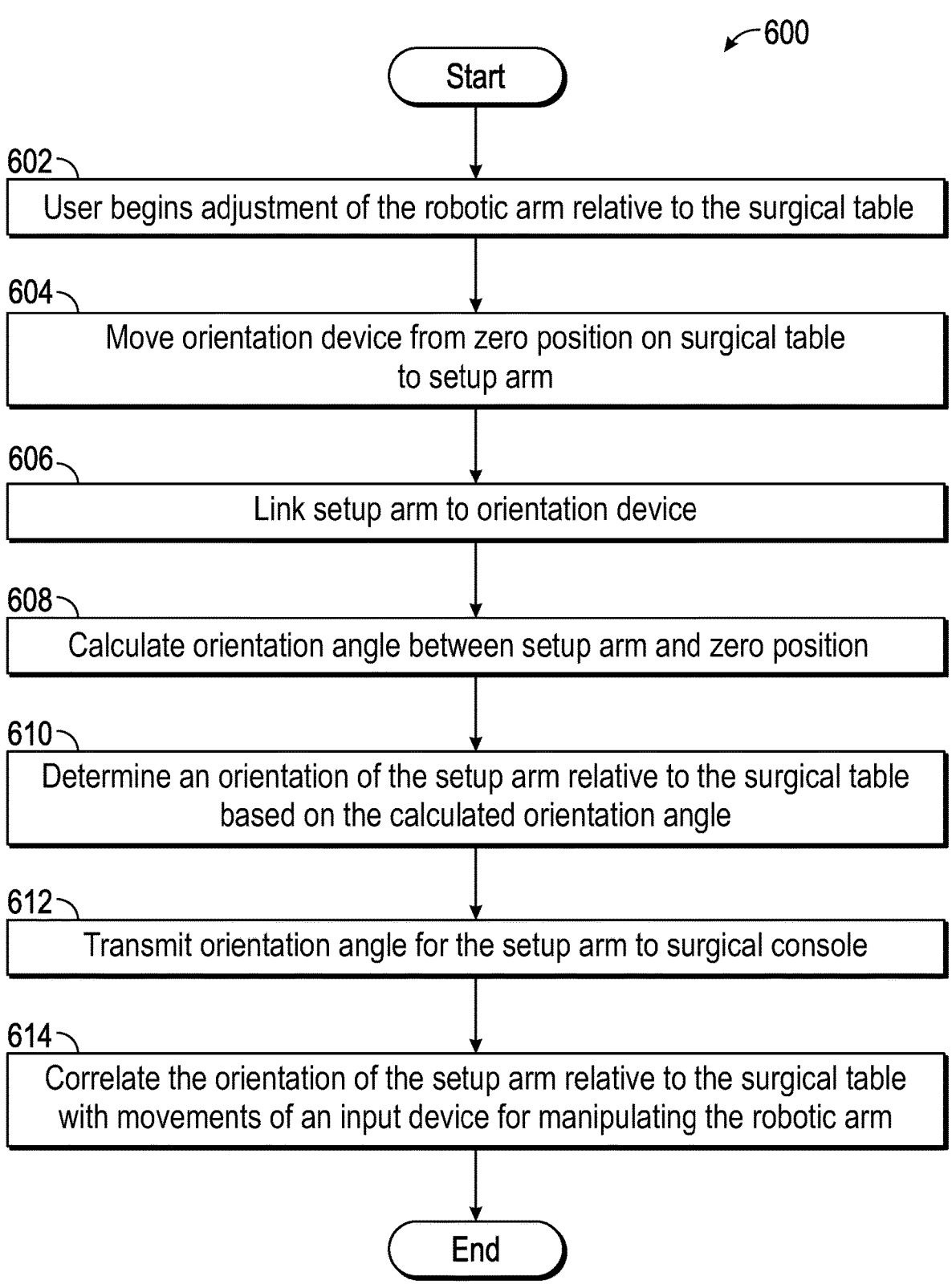
FIG. 8 is a flowchart illustrating a method for registering a setup arm with a surgical table of the surgical robotic system of FIG. 1 according to the present disclosure.

FIG. 8 depicts a flow chart 600 of an illustrative method for registering alignment of a robotic arm 40 with the surgical table 100, which is described in connection with FIGS. 5-7. When setting up the surgical robotic system 10 at step 602, a user may be shown instructions for positioning the movable cart 60, which includes the setup arm 62 (e.g., the first setup arm 621), robotic arm 40, and surgical instrument 50, adjacent to the surgical table 100. The user then adjusts the setup arm 62 or the movable cart 60 to align the setup arm 62 with the surgical table 100. A single setup arm 62 may be oriented in step 602, or multiple setup arms 62 may be orientated in step 602.

In step 604, once a user adjusts the setup arm 62 or the movable cart 60 relative to the surgical table 100, the orientation device 400 is placed at a zero position 110 on the surgical table 100, for storage of the zero position 110 in the memory of the orientation device 400. The zero position 110 is a reference point (e.g., on the surgical table 100) which is utilized for calculating the orientation angles (e.g., θa, θb, θc, θd . . . θn) between each setup arm 62 (e.g., the first setup arm 621, the second setup arm 622, the third setup arm 623, the fourth setup arm 624, etc.) and the reference point on the surgical table 100. After the zero position 110 is stored in the memory of the orientation device 400, the orientation device 400, in step 604, is moved from the zero position 110 to the setup arm 62 (e.g., the first setup arm 621). Step 604 may include resting the orientation device 400 against the alignment member 67b of the setup arm 62 to ensure proper alignment of the orientation device 400 relative to a surface of the setup arm 62.

In step 606, the orientation device 400 is communicatively linked to the setup arm 62 (e.g., the first setup arm 461). In an aspect, once the orientation device 400 is moved to the proximity of the setup arm 62, the orientation device 400 is automatically linked to the setup arm 62 via the identification device 67a of the setup arm 62 (e.g., an RFID tag or near field communication device readable by the orientation device 400), for example, when the orientation device 400 is rested against alignment member 67b. In another aspect, the setup arm 62 includes an optically readable identification device 67a, such as a bar code or QR code, which is readable by the orientation device 400 to link the orientation device 400 to the setup arm 62. Once the orientation device 400 is linked to the setup arm 62 and placed against the alignment member 67b, in step 608, the orientation angle (e.g., θa) between the linked setup arm 62 (e.g., the first setup arm 621) and zero position 110 of the surgical table 100 is calculated either by the orientation device 400 itself or another component of the surgical robotic system 10. The calculation may be triggered automatically upon being linked with the setup arm 62 or may be triggered upon manual activation by a user. In an aspect, the orientation device 400 or other component of the surgical robotic system 10 may be prevented from calculating the orientation angle in step 608 unless it is confirmed that the brakes 68 of the movable cart 60 are activated (e.g., engaged) to prevent inadvertent movement of the movable cart 60 during or after the orientation angle is calculated. In an aspect, the user may manually confirm that the brakes 68 are activated by inputting a manual confirmation. Alternatively, the brakes 68 may include a sensor (not shown) for the movable cart 60 to communicatively confirm the current state of the brakes 68, that is, whether the brakes 68 are activated or not.

In step 610, the orientation device 400 or other component of the surgical robotic system 10 determines the orientation of the setup arm 62 (e.g., the first setup arm 621) relative to the surgical table 100 based on the calculated orientation angle (e.g., θa) between the linked setup arm 62 (e.g., the first setup arm 621) and the zero position 110 of the surgical table 100. If more than one robotic arm 40 is being utilized, then the user may move the orientation device 400 to the next setup arm 62 (e.g., from the first setup arm 621 to the second setup arm 622) for acquiring the orientation angle of the next setup arm 62. In step 612, the orientation device 400 or other component of the surgical robotic system 10 transmits the determined orientation of the setup arm 62 (e.g., the first setup arm 621), determined in step 610, to the surgical console 30.

In step 614, the surgical console 30 correlates the orientation of the setup arm 62 (e.g., the first setup arm 621) relative to the surgical table 100 with movements of the handle controllers 38a, 38b for manipulating the robotic arm 40 associated with the setup arm 62. Step 614 may be carried out immediately subsequent to step 612, or step 614 may be carried out after all orientation angles (e.g., θa, θb, θc, θd) for each linked setup arm 62 (e.g., first setup arm 621, second setup arm 622, third setup arm 623, fourth setup arm 624) is calculated by either the orientation device 400 or another component of the surgical robotic system 10. Thus, in an aspect, after the orientation angle θa of the first setup arm 621 is calculated, the user may move the orientation device 400 to the second setup arm 622, where steps 606, 608, 610, and 612 are carried out for calculating the orientation angle θb of the second setup arm 622 by either the orientation device 400 or another component of the surgical robotic system 10. Additionally, after the orientation angle θb of the second setup arm 622 is calculated, the user may move the orientation device 400 to the third setup arm 623, where steps 606, 608, 610, and 612 are carried out for calculating the orientation angle θc of the third setup arm 623 by either the orientation device 400 or another component of the surgical robotic system 10, and after the orientation angle θc of the third setup arm 623 is calculated, the user may move the orientation device 400 to the fourth setup arm 624, where steps 606, 608, 610, and 612 are carried out for calculating the orientation angle θd of the fourth setup arm 624 by either the orientation device 400 or another component of the surgical robotic system 10. These steps may be repeated for any number of setup arms 62 being used with the surgical robotic system 10. As each orientation angle (e.g., θa, θb, θc, θd) is calculated, or after all orientation angles (e.g., θa, θb, θc, θd) are calculated, step 614 may be carried out by the surgical console 30 to correlate the respective orientations of each setup arm 62 relative to the surgical table 100 with movements of handle controllers 38, 38b for manipulating the respective robotic arm 40 associated with the setup arm 62.

In addition to correlating the orientation of the setup arm 62 relative to the surgical table 100 with movements of handle controllers 38, 38b for manipulating the respective robotic arm 40 associated with the setup arm 62, the surgical console 30 may utilize the data corresponding to the respective orientation angles θa, θb, θc, θd . . . θn to determine whether the movable carts 60 are sufficiently spaced apart so as to avoid the possibility of a collision between components of any two movable carts 60. In particular, the surgical console 30 may determine whether the movable carts 60 are spaced apart by a predetermined distance, and if not, notify the user (e.g., via an audible, visual, and/or tactile notification) that the movable carts 60 are positioned too close together and may collide as the respective robotic arms 40 are moved.

The surgical robotic system 10 according to the present disclosure is configured to perform a registration process to correlate (e.g., register) the orientation of each of a plurality of movable carts 60 and attached robotic arm 40 relative to a central point in space, such as a surgical table 100 (FIG. 7) using the orientation angles (e.g., θa, θb, θc, θd) calculated for each setup arm 62. During the registration process, the surgical robotic system 10 determines the relative orientation of the setup arms 62 of the robotic arms 40 using the orientation device 400 as described above. The surgical robotic system 10, and in particular the computer 21 of the control tower 20, is configured to execute an algorithm that computes the registration angles for each movable cart 60 based on the orientation angle θ as input from the orientation device 400 or other components of the surgical robotic system 10 as described above with respect to FIGS. 5-8.

Furthermore, registered and unregistered notifications are sent out to the control tower 20 and the surgical console 30 to indicate the registration state of each movable cart 60. Registration is also confirmed by the operating room staff before performing tele-robotic operation of the surgical robotic system 10.

The main cart controller 41a is configured to perform the registration process and handles setting various registration states for the movable cart 60 and the robotic arm 40. In one embodiment, the main cart controller 41a is configured to set the movable cart 60 to a registered state when the following conditions are met: 1) one or more of the brakes 68 are activated to prevent the movement of the movable cart 60 (via a sensor communication or via a manual input); 2) the robotic arm 40 attached to the movable cart 60 is aligned relative to the surgical table 100 and the orientation angle is received from the orientation device 400; and 3) the surgical instrument 50 of the robotic arm 40 is coupled to an access port or trocar (not shown) that is inserted into a patient's abdominal cavity (via a sensor communication or via a manual input).

Conversely, the main cart controller 41a is configured to set the movable cart 60 to an unregistered state when the following conditions are met: 1) one or more of the brakes 68 are deactivated to allow the movement of the movable cart 60; and 2) the surgical instrument 50 of the robotic arm 40 is decoupled to the port or trocar.

The controller 21a coordinates communication between operating room team interface (ORTI) and the main cart controller 41a of the movable cart 60. The ORTI is displayed on the display 23 of the control tower 20 as well as the second display 34. The controller 21a is also configured to confirm that each of the movable carts 60 is registered before teleoperation is enabled for the robotic arm 40 and is further configured to determine when two adjacent robotic arms 40 are too close to each other based on the registered angle. The controller 21a receives the registration status of each movable cart 60 and publishes data to the main cart controller 41a of each of the movable cart 60 and the ORTI indicating which robotic arms 40 have been user-confirmed, and warnings (e.g., audible, visual, and/or tactile) if the robotic arms 40 are placed too close together.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
   a movable cart positioned relative to a surgical table and including a setup arm and a robotic arm;
   an orientation device including a memory and a computer configured to:
   store a zero position of the surgical table upon being placed at the zero position;
   link with the robotic arm;
   store a position of the setup arm upon being placed at the position of the setup arm; and
   calculate an orientation angle between the setup arm and the surgical table based on the stored zero position of the surgical table and the stored position of the setup arm; and
   a surgical console including an input device communicatively coupled to the robotic arm and configured to control movement of the robotic arm, wherein the surgical console is configured to correlate the calculated orientation angle of the setup arm with movements of the input device for controlling movement of the robotic arm.

2. The surgical robotic system according to claim 1, wherein the setup arm includes an identification device readable by the orientation device for linking the orientation device to the setup arm, the identification device including at least one of a near field communication chip or an optically readable code.

3. The surgical robotic system according to claim 1, wherein the setup arm includes an alignment member configured to align the orientation device to the setup arm upon placement of the orientation device at the position of the setup arm.

4. The surgical robotic system according to claim 1, wherein the surgical console is configured to determine whether two adjacent robotic arms are distanced a predetermined distance apart based on the calculated orientation angle of the setup arm.

5. A surgical robotic system comprising:

a surgical table;

a first movable cart positioned relative to the surgical table and including a first setup arm;

a second movable cart positioned relative to the surgical table and including a second setup arm;

an orientation device including a memory and a computer configured to:

store a zero position of the surgical table upon being placed at the zero position;

link with the first setup arm;

store a position of the first setup arm upon being placed at the position of the first setup arm;

calculate an orientation angle between the first setup arm and the surgical table based on the stored zero position of the surgical table and the stored position of the first setup arm;

link with the second setup arm;

store a position of the second setup arm upon being placed at the position of the second setup arm; and calculate an orientation angle between the second setup arm and the surgical table based on the stored zero position of the surgical table and the stored position of the second setup arm.

6. The surgical robotic system according to claim 5, wherein the first setup arm includes a first identification device readable by the orientation device for linking the orientation device to the first setup arm and the second setup arm includes a second identification device readable by the orientation device for linking the orientation device to the second setup arm.

7. The surgical robotic system according to claim 6, wherein the first identification device and the second identification device include at least one of a near field communication chip or an optically readable code.

8. The surgical robotic system according to claim 5, wherein the first movable cart includes a first brake and the second movable cart includes a second brake.

9. The surgical robotic system according to claim 8, further comprising a cart controller in communication with the orientation device, wherein the cart controller is configured to:

identify the first movable cart as registered in response to the first brake being engaged and receipt of the orientation angle of the first setup arm; and identify the second movable cart as registered in response to the second brake being engaged and receipt of the orientation angle of the second setup arm.

10. The surgical robotic system according to claim 5, wherein the first setup arm includes a first alignment member configured to align the orientation device to the first setup arm upon placement of the orientation device at the position of the first setup arm and the second setup arm includes a second alignment member configured to align the orientation device to the second setup arm upon placement of the orientation device at the position of the second setup arm.

11. The surgical robotic system according to claim 5, further comprising a surgical console including an input device communicatively coupled to a first robotic arm of the first movable cart and second robotic arm of the second movable cart, the surgical console configured to:

receive the calculated orientation angle of the first setup arm and the calculated orientation angle of the second setup arm from the orientation device;

correlate the calculated orientation angle of the first setup arm with movements of the input device for controlling movement of the first robotic arm; and correlate the calculated orientation angle of the second setup arm with movements of the input device for controlling movement of the second robotic arm.

12. The surgical robotic system according to claim 5, wherein the computer is configured to determine whether the first movable cart and the second movable cart are spaced apart by a predetermined distance based on the orientation angle of the first setup arm and the orientation angle of the second setup arm.

13. A method of registering a setup arm with a surgical table, the method comprising:

receiving zero position data from an orientation device;

linking the orientation device to a first setup arm of a first movable cart positioned relative to a surgical table;

calculating, by a computer, an orientation angle of the first setup arm relative to the surgical table based on at least the zero position data;

linking the orientation device to a second setup arm of a second movable cart positioned relative to the surgical table; and calculating, by the computer, an orientation angle of the second setup arm relative to the surgical table based on at least the zero position data.

14. The method according to claim 13, wherein the first setup arm includes a first identification device readable by the orientation device for linking the orientation device to the first setup arm and the second setup arm includes a second identification device readable by the orientation device for linking the orientation device to the second setup arm.

15. The method according to claim 14, wherein the first identification device and the second identification device include at least one of a near field communication chip or an optically readable code.

16. The method according to claim 13, wherein the first movable cart includes a first brake and the second movable cart includes a second brake.

17. The method according to claim 16, further comprising:

identifying the first movable cart as registered in response to the first brake being engaged and receipt of the orientation angle of the first setup arm; and identifying the second movable cart as registered in response to the second brake being engaged and receipt of the orientation angle of the second setup arm.

18. The method according to claim 13, further comprising determining whether the first movable cart and the second movable cart are spaced apart by a predetermined distance based on the orientation angle of the first setup arm and the orientation angle of the second setup arm.

19. The method according to claim 13, wherein the first setup arm includes a first alignment member configured to align the orientation device to the first setup arm upon placement of the orientation device at the position of the first setup arm and the second setup arm includes a second alignment member configured to align the orientation device to the second setup arm upon placement of the orientation device at the position of the second setup arm.

20. The method according to claim 13, further comprising:

delivering the calculated orientation angle of the first setup arm and the calculated orientation angle of the second setup arm to a surgical console including an input device configured to control movement of a first robotic arm of the first movable cart and a second robotic arm of the second movable cart;

correlating the calculated orientation angle of the first setup arm with movements of the input device for controlling movement of the first robotic arm; and correlating the calculated orientation angle of the second setup arm with movements of the input device for controlling movement of the second robotic arm.

* * * * *